United States Patent [19]

Iest

[11] Patent Number: 5,169,236

[45] Date of Patent: Dec. 8, 1992

[54] DIGITAL SPA THERMOMETER

[76] Inventor: Lynn D. Iest, 1870 Hill Road Ter., Boise, Id. 83702

[21] Appl. No.: 579,591

[22] Filed: Sep. 10, 1990

[51] Int. Cl.⁵ .................. G01K 1/00; G01K 13/00; G01K 1/08

[52] U.S. Cl. ................... 374/156; 374/142; 4/496

[58] Field of Search ............. 374/156, 208, 109, 136, 374/170, 142, 102; 4/496, 541, 542, 543, 544; 204/400, 153.1, 153.21, 433, 420

[56] References Cited

U.S. PATENT DOCUMENTS

| | | | |
|---|---|---|---|
| 2,901,907 | 9/1959 | Ashcroft | 374/141 |
| 2,913,903 | 11/1959 | Fried | 374/141 |
| 3,054,096 | 9/1962 | Peritz | 340/244 |
| 3,585,991 | 6/1971 | Balamuth | 4/541 |
| 3,616,272 | 10/1971 | Goerg et al. | 374/141 |
| 3,683,353 | 8/1972 | Miller | 340/566 |
| 3,743,930 | 7/1973 | Fathauer | 374/170 |
| 3,873,446 | 3/1975 | Campbell | 374/141 |
| 3,961,531 | 6/1976 | Peng | 374/208 |
| 3,965,743 | 6/1976 | Turner | 374/142 |
| 3,969,712 | 7/1976 | Butman et al. | 340/261 |
| 4,017,842 | 4/1977 | Vineyard | 340/541 |
| 4,030,361 | 6/1977 | Fortune | 374/156 |
| 4,109,527 | 8/1978 | Goode, Jr. | 374/142 |
| 4,112,764 | 9/1978 | Turner | 374/142 |
| 4,169,378 | 10/1979 | Di Marchi et al. | 374/156 |
| 4,187,502 | 2/1980 | Beverly et al. | 340/566 |
| 4,218,875 | 8/1980 | Rothman | 368/73 |
| 4,237,562 | 12/1980 | DuPont | 4/543 |
| 4,282,591 | 8/1981 | Andreuccetti | 374/142 |
| 4,338,174 | 7/1982 | Tamura | 374/142 |
| 4,503,563 | 3/1985 | Johnson | 455/351 |
| 4,506,371 | 3/1985 | Cross et al. | 374/136 |
| 4,601,589 | 7/1986 | Meisner | 374/208 |
| 4,702,614 | 10/1987 | Copley et al. | 368/72 |
| 4,730,941 | 3/1988 | Levine et al. | 374/170 |
| 4,738,549 | 4/1988 | Plimpton | 374/208 |
| 4,771,791 | 9/1988 | Kubouchi | 128/736 |
| 4,775,854 | 10/1988 | Cottrell | 340/573 |
| 4,780,917 | 11/1988 | Hancock | 4/544 |
| 4,821,445 | 4/1989 | Bass | 43/4.5 |

Primary Examiner—William A. Cuchlinski, Jr.
Assistant Examiner—Diego F. F. Gutierrez
Attorney, Agent, or Firm—William J. Bethurum

[57] ABSTRACT

A floating digital display thermometer for a hot tub, spa or swimming pool, having a motion-sensitive switch responsive to wave action or intentional manipulation. The components are arranged within a watertight housing to ensure that a digital display always remains up to ensure easy viewing. Circuitry is provided for converting temperature readings to a digital display, and for indicating other functions such as time and date, and for providing alarm and music capabilities. Manually-activated membrane switches may be provided to activate various functions of the device. Furthermore, the thermometer is also capable of measuring and displaying the PH and the oxidation reduction potential of the liquid in the spa or swimming pool.

7 Claims, 3 Drawing Sheets

DIGITAL SPA THERMOMETER

CROSS-REFERENCE TO OTHER APPLICATIONS

This application is derived from application Ser. No. 346,366, filed Apr. 27, 1989, now abandoned, which in turn was a continuation of parent application Ser. No. 191,603, filed May 9, 1988, now abandoned.

BACKGROUND ART

This invention relates to a solid state digital thermometer having a number of additional useful features for use in a spa, hot tub, bathtub or swimming pool. Spas are typically utilized out-of-doors away from readily available clocks or time pieces. Because spas are typically operated and used at an elevated temperature, it is advantageous to have readily available a thermometer which enables users to determine the water temperature of the spa.

The usefulness of a floating spa thermometer is disclosed in, for instance, U.S. Pat. No. 4,503,563 in which a combination light, temperature probe and radio is adapted to float within a spa. A handle enables it to be used as a portable lantern or radio. A somewhat more primitive device is disclosed in U.S. Pat. No. 4,435,095, wherein a glass mercury thermometer is provided to measure the temperature of a hot tub.

Digital display thermometers are well-known. For example, U.S. Pat. No. 4,444,517 discloses an electronic clinical thermometer having a magnetic reed switch requiring that, once activated, the thermometer must be placed in a magnetic field to break the contact to the battery. The device is watertight and is not provided with illumination means for use at night. Also, U.S. Pat. No. 4,601,589 is an electric thermometer powered by a solar cell having a digital display of temperature.

Lastly, a pair of swimming pool alarms are disclosed in U.S. Pat. Nos. 3,969,712 and 3,054,096. Both devices utilize motion-sensitive switches responsive to waves in the pool, setting off alarms to indicate that, for instance, a child has fallen into the pool.

SUMMARY OF THE INVENTION

The apparatus of the present invention is intended primarily as a thermometer for measuring the temperature of spas, hot tubs and pools. The device is adapted to float on the water surface and to indicate the temperature either automatically responsive to activation of a motion-sensitive switch, or manually responsive to a manual switch. The device is enclosed in a buoyant, watertight housing which may be in the form either of clear plastic or provided with various colors, scenes or commercial advertising. A temperature probe extending through the buoyant housing is adapted to measure the water temperature and convey such measurement to a temperature on a digital display screen. The device is battery operated, with a majority of the weight of the apparatus below the centerline of the apparatus so as to maintain proper orientation of the device with the digital display unit in an "up" position.

The movement sensitive switch may be any type of switch which will become activated upon a rapid movement of or shock to the apparatus by one wishing to observe one or more of its functions. Alternatively, a manually activated switch may be provided to activate the temperature probe without resort to the movement sensitive switch.

In addition to the temperature probe, the device may be provided with additional features, such as a light source for viewing in darkness, time/date means for indication in the digital display means, an alarm to indicate passage of a predetermined period of time, and means to emit musical tones when one of the other functions is activated. Each of these additional features may be provided with a manual switch for activation when desired.

The device is provided with timers such that upon activation of any of the features, they will automatically be turned off after a predetermined time lapse so as to conserve battery power. Additionally, the motion-sensitive switch may be provided with means to continue illumination of the appropriate temperature beyond when the motion-sensitive switch has been opened by a movement opposite that which closed the switch initially.

Therefore, it is an object of the present invention to provide a floating watertight thermometer for measuring water temperature. Temperature of the water measured by this device is displayed in a digital display located on the upper surface of the device.

It is a further object of this invention to provide means to turn on and turn off the thermometer, and various other features, either automatically through motion-sensitive switches, or manually through manually activated switches. Other objects and advantages of this invention will become apparent after consideration of the following drawings and descriptions.

DETAILED DESCRIPTION OF THE INVENTION

Figure 1:
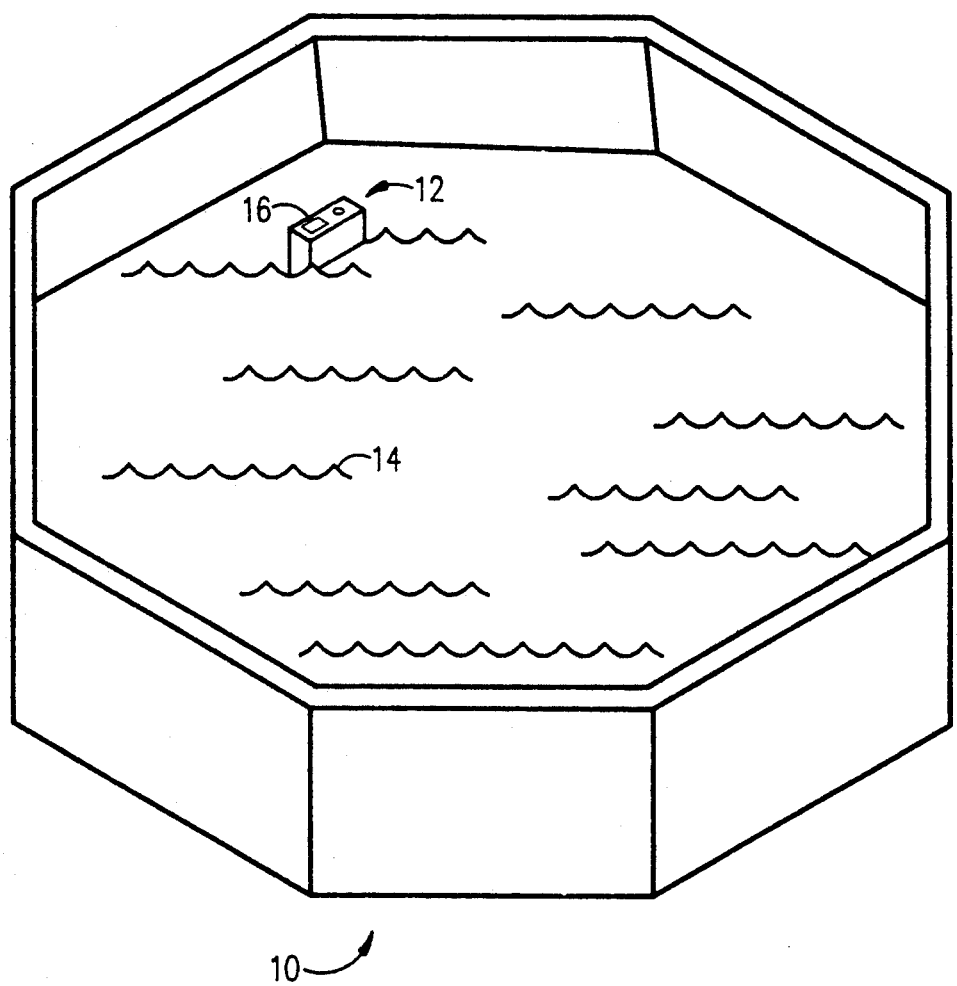
FIG. 1 is an isometric view of the apparatus of the present invention in a spa.

Referring now to the drawings, FIG. 1 illustrates a spa or hot tub, generally designated 10 within which is floating the thermometer 12 of the present invention in a body of water 14. As illustrated, the thermometer of the present invention floats in an upright position with a digital display 16 facing upwardly for easy viewing.

Figure 2:
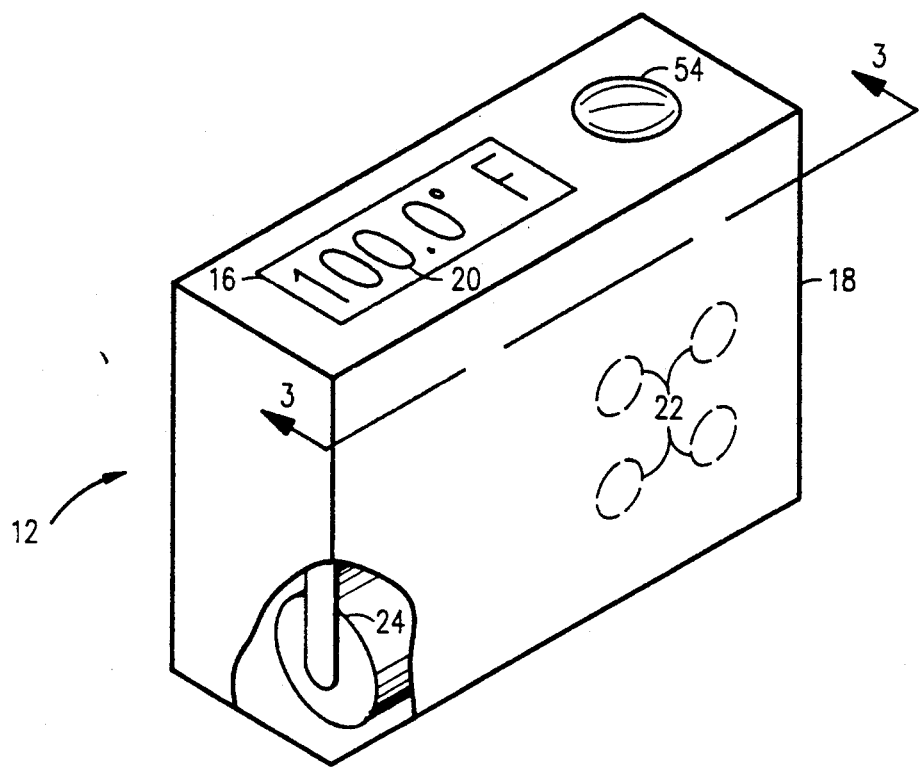
FIG. 2 is a close-up view of the apparatus of FIG. 1.

More specifically, FIG. 2 illustrates the apparatus of the present invention in greater detail. As illustrated, the apparatus comprises an exterior housing 18, which must be watertight in order to protect the internal components and circuitry of the apparatus. The digital display window 16 displays a number of numerals of letters 20 indicating the temperature, time, date or other useful information. The digital numerals and/or letters are preferably provided in the form of a liquid crystal display (LCD), but may other types of displays which are well-known to those skilled in this art. The housing 18 may be provided with a number of manual switch means 22 to manually control or activate the display of a number of functions, as set forth in greater detail below.

Because the housing 18 is airtight, it will in most cases float upon the surface of a body of water within spa 10. However, additional buoyancy may be added by lining or packing the interior of housing 18 with buoyant materials. The housing 18 may be encased in a translucent plastic, or the housing 18 may be itself either a translucent or colored material. Art work may be provided on the exterior of housing 18 (such as tropical beach scenes or advertising) before encasing in translucent materials.

As illustrated, the device is provided with one or more batteries 24 which provide power for the various electronic functions of the device, as well as illumination of the display 16. It is contemplated that the battery 24 will be encased in the housing 18 without means for replacing the battery after its useful life has expired. Any means to access the battery for replacement increases the risk of leaks into the interior of housing 18. The battery is preferably a miniaturized lithium-style long life battery commonly found in watches, hearing aids, etc. Because the features of the present invention are only activated periodically, it is anticipated that the useful life of such batteries in the instant invention will be at least 2 to 4 years. Alternatively, means may be provided to recharge the batteries, if the batteries so permit. If conventional alkaline batteries (as depicted in FIG. 2) are utilized, an access port through housing 18 may be desirable in order to replace spent batteries. Obviously, such port (not shown in the drawings) must be watertight to ensure no leakage of the housing. Such batteries may be necessary to maintain proper orientation of the apparatus.

Figure 3:
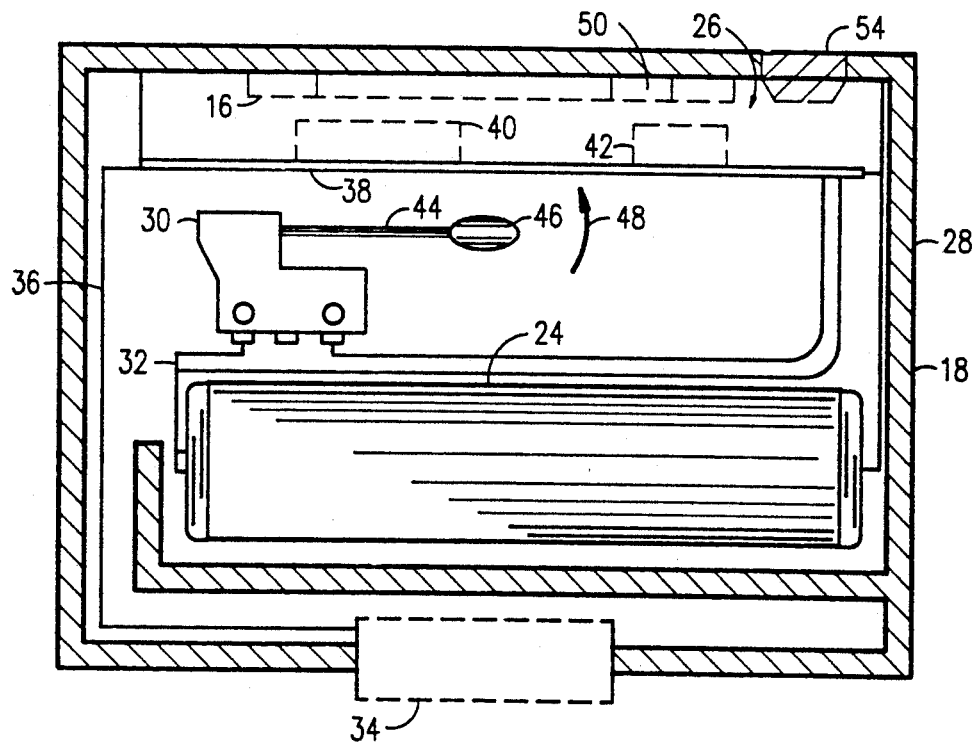
FIG. 3 is a sectional view taken along lines 3—3 of FIG. 2.

FIG. 3 illustrates the device of the present invention in greater detail. As illustrated, the battery 24 is interconnected to thermometer 26 with wire 28, and also to the microswitch 30 by wire 32. A temperature probe 34 is secured in or through the housing 18 so as to be in contact with the water upon which the device floats. The temperature probe 34 is interconnected to the thermometer 26 by wire 36. The battery 24, temperature probe 34, thermometer 26 and microswitch 30 are all interconnected by a conventional circuitry assembly 38. Additionally, a temperature conversion assembly 40 and timing circuitry 42 are mounted to the circuit assembly 38.

In operation, the apparatus of the present invention is typically in an "off" condition due to the fact that the microswitch 30 is a normally "open" switch. As illustrated, the microswitch 30 is a weighted microswitch having an arm 44 with a weight 46 on the end thereof. One of the contact points (not shown) of switch 30 is affixed to the end of arm 44 to be normally in the position illustrated in FIG. 3. A shock or rapid movement of the apparatus causing the weight 46 to move upwardly in the direction of arrow 48 closes the contact points within switch 30, thereby providing power from battery 24 to the various electrical components of the device. When the microswitch 30 is closed and the device is activated, the temperature conversion assembly 40 is activated, converting the temperature reading from thermometer 26 to the digital number displayed in display 16. The LCD display 16 is illuminated by the subminiature lamp 50. The device may be programmed such that while the temperature conversion is in progress, the numerals displayed in the display 16 will flash; when the conversion is complete, the numerals 20 are on continuously, indicating the current water temperature. After a predetermined period of time, the timing element 42 will complete its countdown sequence and turn off the LCD display 16 and subminiature lamp 50.

As illustrated in FIG. 3, the battery 24 comprises a substantial portion of the weight of apparatus 12, and is located in the lower portion of housing 18. Therefore, the center of mass of the apparatus 12 is below the centerline of the apparatus, thereby insuring that the digital display 16 will remain in an upright position for viewing. When a relatively small watch-type battery is utilized herein, additional weights may be placed in the bottom of the device to ensure proper weight distribution to maintain the digital display up.

Figure 4:
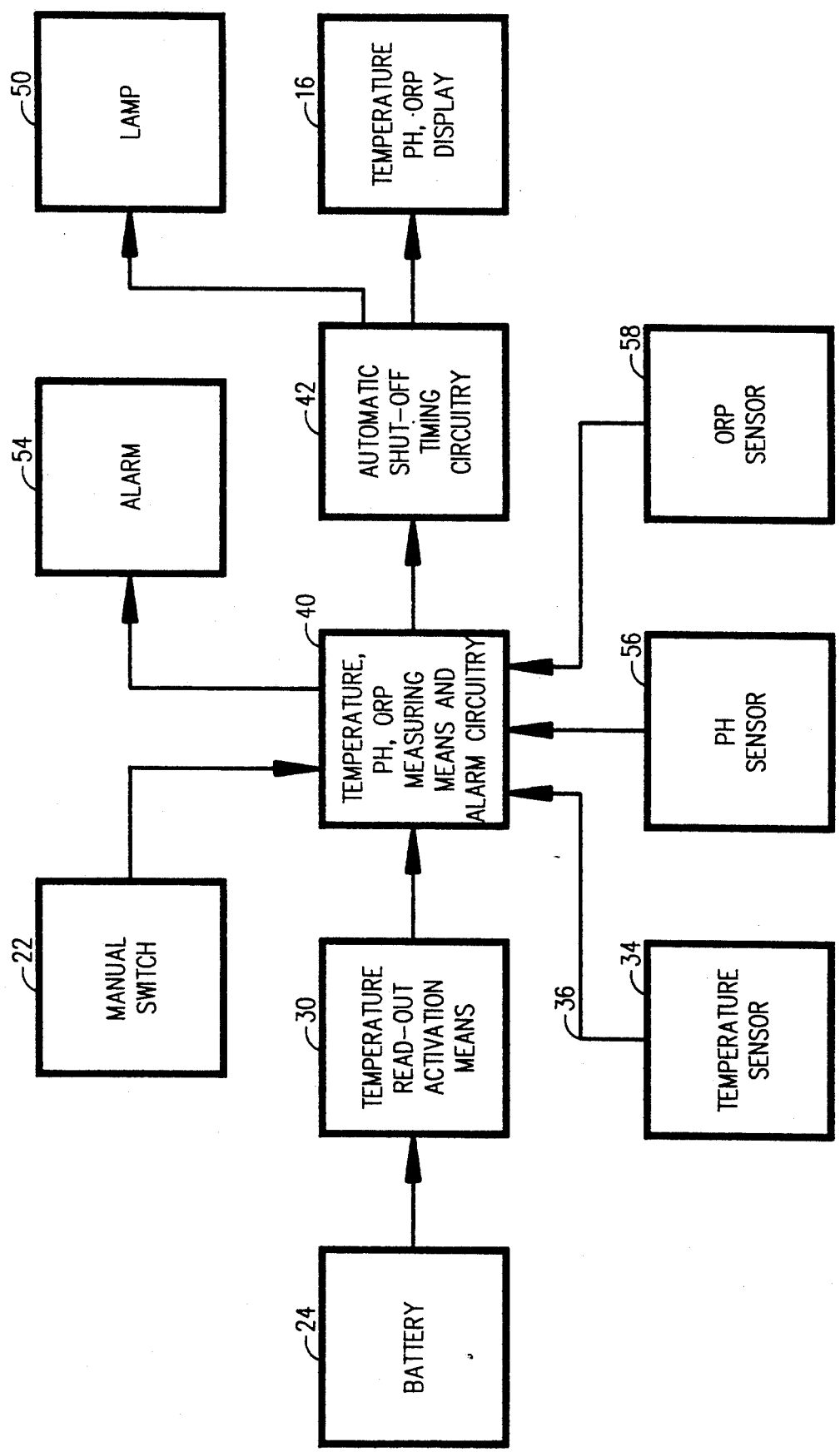
FIG. 4 is a functional block diagram which shows the various electrical interconnections between the electrical components which may be incorporated in the structure of FIGS. 2 and 3.

Referring now to FIG. 4, this figure has been added herewith in order to illustrate the functional relationships between the various components shown in FIGS. 2 and 3 above. In addition, the new matter added by way of FIG. 4 relates to the PH sensing means 56 and to the oxidation reduction potential (ORP) sensing means 58 as will be described in further detail below. However, apart from the newly added functional elements of the PH sensing means 56 and the ORP sensing means 58, the remaining functional block diagram elements shown in FIG. 4 find a full and complete basis in the above description of FIGS. 2 and 3. These functional elements have been added by way of FIG. 4 of the present application in order to provide the reader with an easier understanding of the particular electrical connections which are made between all of the components shown in FIG. 4 in order to allow the novel circuit operation to take place in a manner to be described.

Referring again to FIG. 4, it will be seen that the battery 24 is connected to provide power to a temperature read out activation means 30, which in FIG. 3 is embodied in the microswitch as indicated. The temperature read out activation means 30 is in turn connected to drive and provide an input signal to temperature, PH, ORP measuring means and alarm circuitry 41. This stage 41 is in turn connected to drive automatic shut-off timing circuitry 43, which as previously indicated is preferably a selected timer having a predetermined time-out period. The automatic shut-off timing circuitry 43 is connected to temperature, PH and ORP display means 16 which is embodied in the form of a digital read out as previously indicated in FIG. 2 above. The automatic shut-off timing circuitry 43 is further connected to a lamp 50 which is constructed adjacent to the temperature, PH and ORP display means 16 in order to provide adequate lighting for the read out display means 16.

The temperature, PH and ORP measuring means and alarm circuitry 40 is further connected to provide an output signal to an alarm means 54 which, as indicated in FIGS. 2 and 3 above, is preferably an audio alarm of any desired type. The temperature, PH and ORP measuring means and alarm circuitry 41 is further connected to manual switching means 22, which in the embodiment of FIGS. 2 and 3 above consists of a plurality of circular shaped manually operated membranes located on the outer walls of the device housing.

The system of FIG. 4 further includes three sensors in the form of temperature sensing means 34, PH sensing means 6, and oxidation-reduction potential (ORP) sensing means 58 which are all connected as shown to drive and provide input signals to the temperature, PH, ORP measuring means and alarm circuitry 41. The temperature sensing means 34 has been previously described in FIG. 3 above as preferably being a temperature probe having the same reference numeral 34 as shown and being connected by way of an electrical connection 36 to the integrated circuit 40 in FIG. 3. The reference 41 is also used in FIG. 4 to identify the temperature, PH, ORP measuring means and alarm circuitry previously described.

It will be appreciated by those skilled in the art that the system of FIG. 4 is extremely versatile and lends itself to the connection of a plurality of diverse sensors such as the temperature, PH and ORP sensors 34, 56, and 58, and the output signals from these diverse sensors 34, 56, and 8 may be parallel processed in the previously described temperature, PH and ORP measuring stage 41 by the use, of, for example, a selected microprocessor for the stage 41 which is capable of simultaneously parallel processing output signals from these three sensor stages 34, 56, and 58. Both PH sensing and oxidation reduction potential sensing are generally well known in the art and various types of both PH or ORP sensors are available for purchase on the commercial market. For example, PH and ORP measuring sensors and instruments have been described in an article in *Pool and Spa News* entitled "Test Kits Marketplace", Vol. 29, No. 4, Feb. 26, 1990 at pages 121-129, and also in data sheets published by the Cole-Parmer Instrument Company of Chicago, Ill. in an article entitled "Instruments For Research, Industry and Education", at pages 487 to 489 and pages 522 to 523. In addition, PH and ORP sensing systems and devices have also been described by Jack Steininger and Wes Kelly of the Aquasense Corporation of Santa Barbara, Calif. in an article entitled "Test Swimming Pool or Spa With One Finger" and published in the *Dealer News* at page 20 in October 1986. All three of the above publications are incorporated herein by reference.

The device of the present invention may be provided with additional electronic circuitry to indicate the time and/or date, and a timed alarm function and musical notes. An internal clock may be provided so that when activated by membrane switch 22, the appropriate time and/or date may be displayed in the digital display 16. An alarm function may be provided with the timing circuitry. By setting a predetermined period of time in the timing circuitry, the alarm 54 will sound to indicate the expiration of the desired timer period. Such feature may be advantageous to ensure that a user of a relatively hot spa does not become overheated by exposure over too great a time. Additionally, a sound-generating apparatus, programmed to play musical notes, may be incorporated into various functions of the apparatus. For instance, the musical notes may be played while temperature conversion unit is activated, or the musical notes may be played at any time the device is "on", to indicate that the device is drawing power from its internal battery.

The device of the present invention as illustrated in the figures, is a motion-sensitive apparatus responsive to waves within the spa 10 or to intentionally-inflicted shock of the apparatus. The timing circuitry ensures that excess battery drain does not occur and that the device is automatically turned off after a predetermined time period.

While a preferred embodiment of the invention has been disclosed, various modes of carrying out the principles disclosed herein are contemplated as being within the scope of the following claims. For example, it is not necessary that the temperature read out activation means 30 be implemented in the form of an acceleration activated microswitch having a movable mass 46 as shown in FIG. 3. Instead, the temperature read out activation means 30 as shown in FIG. 4 above may, for example, be implemented in the form of a detector operative to respond to an infrared or radio signal generated in the vicinity of a pool or spa merely by the turning on of a switch or the like. Alternatively, the digital spa thermometer described above may be provided with a small antenna on its outer housing, which is in turn coupled to a slightly detuned LC resonant circuit and accompanying detector and amplifier. Using such circuitry, a person coming within a predetermined distance of the antenna will, by body capacitance, change the lumped capacitance of the antenna and thereby tuning the LC resonant circuit to resonance and enabling the output signal passed therethrough and detected to be used as an activating signal output from the stage 30 shown in FIG. 4. Such a detected and amplified signal could in turn be used to activate the temperature, PH, ORP measuring means and alarm circuitry 41 as previously described. Finally, it is not essential that the digital display 16 shown in FIG. 2 of the drawings be mounted on a single slanted surface of the device 12. Instead, this display 16 may, for example, be shown on both of two adjacent V-shaped slanting surfaces, or even on four adjacent and orthogonal surfaces which face, respectively, four orthogonal directions so that the digital read out number 20 of the spa or pool temperature may be easily seen by a person positioned at any location around the periphery of the pool or spa into which the hand held device 12 has been introduced. Therefore, it is to be understood that the above and other design modifications are clearly within the scope of the following appended claims.

I claim:

1. A floating digital display apparatus for use in a spa or hot tub, comprising:
    a. a watertight buoyant housing having digital display means on an upper surface thereof;
    b. a temperature probe mounted in the exterior of said housing for sensing the temperature of water in said spa or hot tub;
    c. temperature conversion means whereby temperature of the water is measured by the temperature probe and converted to a digital signal displayed on the digital display in the form of numeral segments;
    d. timing circuitry for maintaining time and date contained within said housing, and automatic shut-off circuitry such that the digital display means is activated for only a predetermined period of time before being automatically shut off;
    e. alarm circuitry and alarm means to indicate expiration of a preset time period;
    f. a plurality of membrane switches on the exterior of said housing enabling manual activation of each of the temperature conversion means, timing circuitry and alarm circuitry;
    g. a movement sensitive switch electrically interconnecting a battery and the temperature probe, such that upon sufficient movement of the housing the movement sensitive switch activates the temperature probe and the digital display means; and
    h. the battery and the movement sensitive switch are arranged such that the center of the mass of the battery and the movement sensitive switch is adjacent the bottom of the buoyant housing and the digital display means is adjacent the top of the buoyant housing to ensure the digital display means remains up when in a floating position.

2. The apparatus as recited in claim 1, wherein the movement sensitive switch is a weighted microswitch.

3. A hand held device operable when introduced into a liquid container to measure the temperature of the liquid in the container from an easy line of sight visual inspection by a person in relatively close proximity to said device, said device including, in combination:
   a. a buoyant housing having top and bottom surfaces thereof adapted to receive active components for said device,
   b. one or more batteries mounted on or adjacent to said bottom surface of said housing and, by gravitational forces, maintaining said housing in an upright position when floating so that said top surface is visible from a line of sight by a person in a nearby location when said device is introduced
   c. temperature read out display means provided on or adjacent to said top surface of said housing.
   d. temperature sensing means connected to temperature measuring means within said housing to provide an indication of the temperature of said liquid, said temperature measuring means being further connected to said temperature read out display means, and
   e. temperature read out activation means connected between said one or more batteries and said temperature measuring means and responsive to an electrical activation signal applied thereto for interconnecting said one or more batteries to said temperature measuring means when it is desired to visually obtain the existing temperature of said liquid in said liquid container, said activation means includes motion responsive means operative in response to the instantaneous motion applied to said device for electrically activating said temperature read out activating means and thereby connecting one or more of said batteries to said temperature measuring means within said housing to thereby initiate a temperature read out indication on said temperature read out display means of the current temperature within said liquid container.

4. The device defined in claim 3 which further includes timing means connected to said temperature read out display means and being activated to start a time out period when said temperature read out display means is activated, whereby said timing means is operable to display the temperature within said liquid container for a predetermined period of time.

5. The device defined in claim 4 which further includes PH sensing means connected to PH measuring means within said housing to provide an indication of the PH level of said liquid.

6. The device defined in claim 4 which further includes oxidation reduction potential sensing means connected to oxidation reduction potential measuring means within said housing to provide an indication of the oxidation reduction potential of said liquid within said liquid container.

7. The device defined in claim 6 which further includes PH sensing means connected to PH measuring means within said housing wherein said temperature measuring means, said PH measuring means, and said oxidation reduction potential measuring means are constructed of a microprocessor said operative for parallel processing of output signals from said temperature sensing means, PH sensing means, and oxidation reduction potential sensing means to provide a high degree of measurement versatility for said device.

* * * * *